United States Patent [19]

Matteson et al.

[11] Patent Number: 4,525,309

[45] Date of Patent: Jun. 25, 1985

[54] LEWIS ACID CATALYSIS OF THE HOMOLOGATION OF BORONIC ESTERS WITH HALOALKYLMETAL REAGENTS

[75] Inventors: Donald S. Matteson, Moscow, Id.; Kizhakethil M. Sadhu, Pullman, Wash.

[73] Assignee: Washington State University Research Foundation, Inc., Pullman, Wash.

[21] Appl. No.: 475,531

[22] Filed: Mar. 15, 1983

[51] Int. Cl.$^3$ ................................................ C07F 5/04
[52] U.S. Cl. ................................................ 260/462 C
[58] Field of Search .................................... 260/462 C

[56] References Cited

U.S. PATENT DOCUMENTS 2,710,252 6/1955 Darling ..................... 260/462 C X
3,078,312 2/1963 Brown ..................... 260/462 C X

OTHER PUBLICATIONS

Sherk et al., J. Org. Chem., vol. 47, pp. 932–935 (1982).
Mori, Tetrahedron, vol. 33, pp. 289–294, (1977).
Mori, Tetrahedron, vol. 30, pp. 4223–4227, (1974).
Taguchi et al., J. Am. Chem. Soc., vol. 96, pp. 3010–3011, (1974).
Rathke et al., Organomet. Chem., vol. 122, pp. 145–149, (1982).
Pearce et al., J. Chem. Ecol., vol. 1, No. 1, pp. 115–124, (1975).
Matteson et al., J. Am. Chem. Soc., vol. 103, pp. 5241, (1981).
Matteson et al., J. Am. Chem. Soc., vol. 102, pp. 7588–7591, (1980).
Bellas et al., Tetrahedron, vol. 25, pp. 5149–5153, (1969).

*Primary Examiner*—Helen M. S. Sneed
*Attorney, Agent, or Firm*—Anthony J. DeLaurentis

[57] ABSTRACT

Boronate complexes are rearranged in the presence of a Lewis acid catalyst to boronic esters, particularly α-haloboronic esters.

27 Claims, No Drawings

LEWIS ACID CATALYSIS OF THE HOMOLOGATION OF BORONIC ESTERS WITH HALOALKYLMETAL REAGENTS

BACKGROUND OF THE INVENTION

The invention relates to the Lewis acid catalyzed rearrangement of boronate complexes to boronic esters. More particularly, the invention relates to the rearrangement of boronate complexes having the general structure (I) to boronic esters having the general structure (II) in accordance with the following equation:

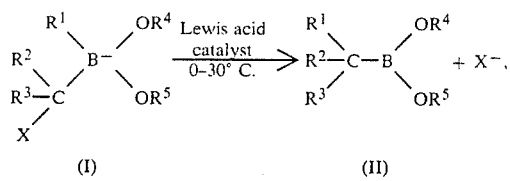

(I)    (II)

where each of $R^1$, $R^4$ and $R^5$ independently, is an organic group as defined more fully hereinbelow, where X is a nucleofugic group, i.e., a group subject to nucleophilic displacement, such as a halogen, and particularly chlorine or bromine, where $R^2$ is H, a lower alkyl or X, where $R^3$ is an organic group (as defined more fully hereinbelow) or X, and where $R^4$ and $R^5$ may be the same or different and may be directly linked, so that the boronic ester is cyclic.

The process of the present invention is particularly useful when $R^4$ and $R^5$, or the linked group $OR^4$—$R^5O$, are chiral groups.

In another aspect, the invention relates to the preparation of α-halo boronic esters, including chiral α-halo boronic esters by the room temperature, Lewis acid catalyzed, conversion or rearrangement of boronic esters (III) to homologous α-halo boronic esters (V) and (VI) by way of intermediate borate anions (IV) which can be formed by reacting the boronic esters (III) at cryogenic temperatures with a dihaloalkylmetal reagent. This aspect of the invention may be characterized by the following equation:

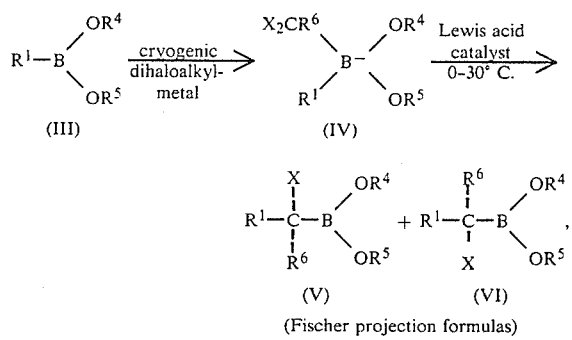

(Fischer projection formulas)

where $R^1$, $R^4$ and $R^5$ are the same as above, X is halogen and $R^6$ is H or lower alkyl.

In still another aspect of the invention, the α-halo boronic esters (V) and (VI) can be prepared by a room temperature Lewis acid catalyzed rearrangement of boronate complexes (IV) which have been prepared at about 0° C. (as opposed to cryogenic temperatures, i.e., about −70° to −100° C.) by reacting the boronic esters (III) with a dihalomethane and a strong, sterically hindered base, such as a metal dialkyl amide, a metal tri-phenylmethane, or a metal bis(trialkylsilyl)amide. This aspect of the invention may be characterized by the following equation:

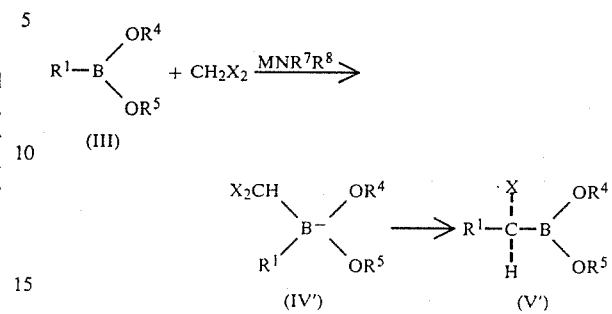

where $R^1$, $R^4$, $R^5$ and X are the same as set forth above, and each of $R^7$ and $R^8$, which may be the same or different, is an alkyl group, preferably a secondary alkyl group such as cyclohexyl or isopropyl.

The present invention is useful for the preparation of a variety of compounds including insect sex attractants, enzyme inhibitors, antibiotics, pharmaceuticals, and other substances having significant biological activity, where the biological activity depends upon the absolute configuration of one or more chiral carbon atoms in the molecule. Thus, an insect sex attractant which can be prepared in accordance with the present invention is chemically identified as (3S,4S)-4-methyl-3-heptanol (from *Scolytus multistriatus*, the European elm bark beetle). Another example is the principal component of the aggregation pheromone of the western pine beetle, *Dendroctonus brevicomis*, which is chemically known as exo-brevicomin. Each of these compounds contains two chiral centers, and the compounds are attractive to the respective insect species only when the chiral centers both have the correct, natural configuration.

The process of the present invention is also useful for the synthesis of an α-acetamido boronic acid, (αS)-α-acetamido-β-phenylethaneboronic acid, which is a potent inhibitor of enzymes known as serine proteases, demonstrated first with chymotrypsin. See Matteson et al., *J. Am. Chem. Soc.*, Vol. 103, pp 5241-2(1981). By use of the present invention, improved yields and purities of the intermediates leading to the α-amido boronic acids can be achieved.

It is to be understood that the novel aspects of the present invention reside in the rearrangement of the various boronate complexes (I) and (IV) at about room temperature in the presence of Lewis acid catalyst which exhibits sufficient acid strength to complex the nucleofugic group X of the boronate complex, yet insufficient acid strength to destroy boronic ester groups associated therewith. Particularly suitable Lewis acid catalysts have been found to include anhydrous zinc chloride and ferric chloride. Mixtures of these and other Lewis acids also may be used.

It is to be understood, further, that the manner in which the boronate complex are prepared is not essential to the present invention, and that complexes formed by any known technique may be employed. For example, as disclosed in Matteson et al., *J. Am. Chem. Soc.*, Vol. 102, pp 7588-7590 (1980) and Matteson et al., *J. Am. Chem. Soc.*, Vol. 102, pp 7590-7591 (1980), the boronate complexes may be prepared by reacting a boronic ester (III) with a dihaloalkylmetal, such as dichloromethyl lithium. The dichloromethyl lithium may be preformed at approximately −100° C. and allowed to react with the boronic ester at that temperature, or the dichloromethyl lithium may be generated in the presence of and rapidly captured by the boronic ester to form the boronate complex at temperatures of about −78° C.

It has also been suggested that dichloromethyl lithium may be prepared by contacting a strong, sterically hindered base, such as an alkali metal dialkylamide, of which lithium dicyclohexylamide is an example, with dichloromethane in the presence of a ketone solvent (Taguchi et al., *J. Am. Chem. Soc.,* Vol. 96, pp 3010–3011 (1974).

Neither of the above Matteson et al. articles suggests the use of a catalyst, and the Taguchi et al. article does not discuss the preparation of boronic esters. However, the Matteson et al. articles indicate that the use of a chiral boronic ester can substantially bias the selectivity of the disclosed non-catalytic process toward formation of the (αS) α-chloro boronic ester at the expense of the (αR) isomer, or vice versa. Specifically, it is disclosed that if

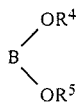

is the cyclic chiral boronic ester group $BO_2C_{10}H_{16}(+)$ which can be prepared from the cis diol derived from (+)-α-pinene by osmium tetroxide catalyzed hydroxylation and which is referred to as "(+)-pinanediol", then the (αS)-α-chloroboronic ester can be produced in significant excess over the (αR)-α-chloroboronic, ratios of (αS)/(αR) in the range 3:1 to 25:1 having been observed with a variety of groups $R^1$ (methyl, n-butyl, cyclohexyl, phenyl, and others). It is further known from Rathke et al., *J. Organomet. Chem.,* Vol. 122, pp 145–149 (1982) that borate complexes (IV) can be generated from dichloromethaneboronic esters,

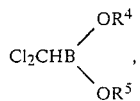

and alkyllithium reagents, $R^9Li$, where $R^9$ is lower alkyl, and that the boronate complexes so formed rearrange to α-chloro boronic esters (V) and (VI).

SUMMARY OF THE INVENTION

The present invention resides primarily in the use of a Lewis acid to catalyze the conversion of boronate complexes to boronic esters. It does not matter how the borate complex is prepared, or whether the counterion for the complex is the lithium cation, the sodium cation or the potassium cation. Similarly, inasmuch as the nucleofuge bromine behaves in much the same manner as chlorine in reactions of the type described, the present invention covers the bromine analogues of all chlorine compounds described and, vice versa.

The use of the Lewis acid catalyst in accordance with the invention promotes the conversion of the intermediate borate anions (I) and (IV) to the desired boronic esters (II), (V) and (VI), and also prevents the interconversion of (V) and (VI) by complexing with the nucleofugic group which catalyzes the interconversion.

A major significance of the present process, therefore, is that where the group

is a suitably chosen chiral boronic ester group, the diastereomer (V) can be obtained almost to the exclusion of (VI), or vice versa, depending on the choice of

It is also significant that the Lewis acid catalysis improves the total yield of the desired boronic esters resulting in nearly quantitative conversions.

The Lewis acid catalysts which may be utilized in the present invention include any Lewis acid of medium strength, defined as a Lewis acid which is strong enough to combine with the nucleofugic groups X to form a complex, but not strong enough to destroy the boronic ester groups $OR^4$ and $OR^5$ (or the linkage $OR^4$—$R^5O$). Examples of Lewis acids which satisfy the above definition include zinc chloride and ferric chloride. "Lewis acid strength" refers to the ability of the substance to complex with species having unshared electron pairs, including ether-type oxygen atoms as well as halide ions.

The amount of Lewis acid to be used may vary depending upon the particular Lewis acid and the reactants involved, but in most cases it has been found that quantities of Lewis acid, particularly zinc chloride or ferric chloride, in the range of 0.5–1.0 mol per mol of (I) or (IV) produce optimum results. In this range of compositions, when $ZnCl_2$ is used, the nucleofugic group released in the rearrangement of (I) or (IV) to (II) or (V) or (VI) is sufficient to complex all of the $ZnCl_2$ as $ZnCL_3^-$ and $ZnCl_4^{2-}$. When excess zinc chloride is used, so that free $ZnCl_2$ remains in substantial concentration toward the conclusion of the reaction, the mixture shows a tendency to darken and the yield and purity of the (II) or (V) or (VI) produced are adversely affected. Furthermore, kinetic studies of the epimerization of (V) to (VI) (where $R^1$=phenyl,

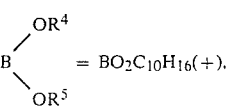

rates followed by polarimetry) have shown that this epimerization is catalyzed by free chloride ion, that the minimum epimerization rate (in tetrahydrofuran as solvent) occurs in the presence of zinc chloride in the stoichiometric amount for formation of $ZnCl_3^-$, that the presence of moderate amounts of $ZnCl_4^{2-}$ accelerates the epimerization of (V) to (VI) only slightly, but that the presence of a slight excess of $ZnCl_2$ greatly accelerates epimerization of (V) to (VI) in solutions concentrated enough to be relevant to preparative reactions. Furthermore, testing of the weaker Lewis acid but good chloride complexing agent, mercuric chloride, failed to yield evidence of any beneficial catalytic effect of practical significance in the conversion of (IV) to (V)

or (VI), though mercuric chloride does greatly retard the epimerization of (V) to (VI). It may be reiterated, therefore, that the essential features of the catalyst to be used in the present invention are that it be a Lewis acid of sufficient acid strength to complex with the nucleofugic group released in the course of the reaction without destroying the boronic ester groups; these criteria being especially well met by zinc chloride and ferric chloride.

DESCRIPTION OF THE INVENTION

The process for preparing boronic esters, especially the α-halo boronic esters, in accordance with the present invention involves the use of a Lewis acid catalyst in the conversion of boronate complexes of the general structure (I) to boronic esters of the general structure (II) in accordance with the following equation:

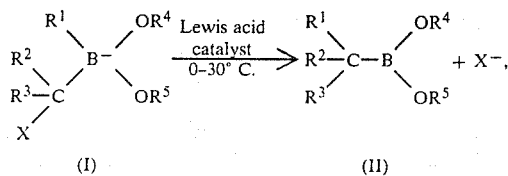

where each of $R^1$, $R^4$ and $R^5$, independently, is a substituted or unsubstituted aliphatic or aromatic group, including but not limited to, primary, secondary, tertiary alkyl groups, vinylic groups, allylic groups, benzylic groups and the like. The functional substituents, if present, may comprise any substituent that will allow the formation of (II), for example alkoxide, ether, ketal, or ester group, so long as the functional substituent does not react faster than the boronic ester group with $CHX_2^-$; in the above formula, X is a nucleofugic group (a group subject to nucleophilic displacement, such as a halide ion, and particularly chloride or bromide); $R^2$ is H, a lower alkyl or X; $R^3$ is X or $R^1$ as defined above; and $R^4$ and $R^5$ may be the same or different and may be directly linked so that the boronic ester is cyclic. The groups $R^4$ and $R^5$, or the linked group $R^4$-$R^5$ preferably comprise a chiral group.

The conversion of (I) to (II) may be carried out at about room temperature (about 20°–30° C.) in a suitable solvent medium. Among the solvents that have been found to be useful are included diethyl ether, tetrahydrofuran, petroleum ether, and the like. Where the group $R^1$ belongs to a class having high migratory aptitude, the optimum temperature may be lower, evidence for efficient conversion of (I) to (II) at −40° to 0° C. having been obtained where $R^1$ is vinyl or phenyl.

In a preferred embodiment, the boronic ester (II) may comprise an α-halo boronic ester (V) or (VI), including chiral α-halo boronic esters, prepared from an intermediate borate ion or complex (IV) which, in turn, may be prepared by reacting a boronic ester (III) with a dihaloalkylmetal reagent in accordance with the following equation:

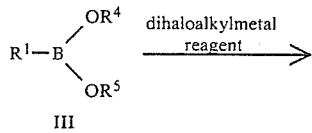

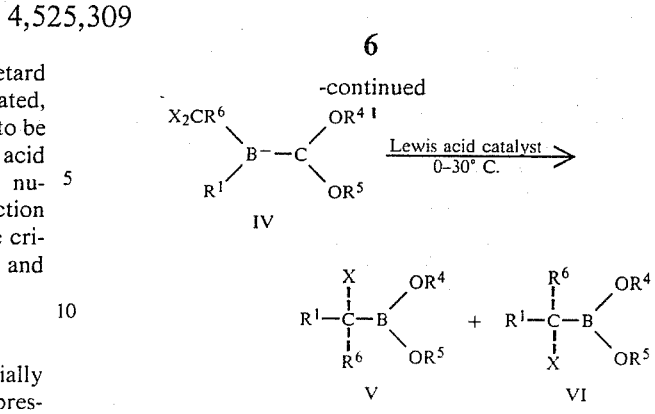

where $R^1$, $R^4$ and $R^5$ are the same as described above, $R^6$ is H or lower alkyl and X is a halogen.

The dihaloalkylmetal reagent can be prepared by any known technique. For example, the dihaloalkylmetal reagent may be preformed at approximately −100° C. by the addition, with stirring under argon, of a hexane solution of n-butyllithium to a tetrahydrofuran solution of dichloromethane. Alternatively, the dihaloalkylmetal can be prepared in situ at about −78° C. by adding a hexane solution of lithium diisopropylamide which has been fluidized with tetrahydrofuran dropwise to a dimethoxyethane solution of dichloromethane and the boronic ester (III). See Matteson et al., *J. Am. Chem. Soc.*, Vol. 102, pp 7588–7590 (1980). In an even more preferred embodiment, the dihaloalkylmetal reagent can be prepared in situ at about 0° C. by reacting in the presence of the boronic ester (III) a dihalomethane and a strong, sterically hindered base, such as lithiotriphenylmethane, an alkali metal bis(trialkylsilyl)amide such as $LiN[Si(CH_3)_3]_2$, $NaN[Si(CH_3)_3]_2$, or $KN[Si(CH_3)_3]_2$, or an alkali metal dialkylamide having the general structure $MNR^7R^8$, where M is lithium, sodium or potassium, and $R^7$ and $R^8$ are the same or different lower alkyl groups. Examples of the alkali metal dialkylamides which may be used include lithium dicyclohexylamide and lithium diisopropylamide. See Taguchi et al., *J. Am. Chem. Soc.*, Vol. 96, pp 3010–3011 (1974).

As indicated above, the present invention is particularly well suited for the Lewis acid catalyzed rearranging of chiral boronate complexes such as those having the general structure:

where

represents a chiral group that is "(S)-directing", for example, boronate complexes derived from (+)-pinanediol (derived from (+)-pinene) or (R,R)-2,3-butanediol, which will yield (αS)-α-haloboronic esters of the general formula:

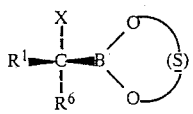

The general structures of (+)-pinanediol (IX) and (R,R)-2,3-butanediol (X) are as follows:

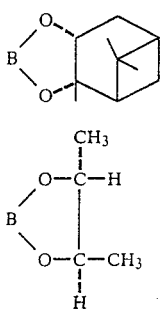

It will be appreciated of course that the enantiomers of these groups, i.e.

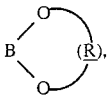

will be formed from boronate complexes derived from (−)-pinanediol or (S,S)-2,3-butanediol, which are "(R)-directing" and yield (αR)-α-haloboronic esters of the general structure:

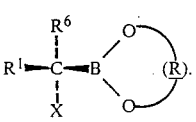

Rearrangements of the above type can be illustrated by the following equation:

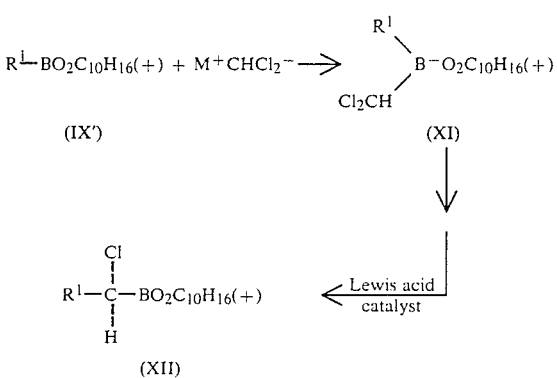

As a result of the high steroselectivity provided by the present invention in the synthesis of α-halo boronic esters, it has been shown that nucleophilic displacement of the halogen (as chloride or bromide) is indeed highly steroselective or stereospecific. If the nucleophile is the alkyl or aryl group derived from a Grignard or organolithium reagent, the product is a boronic ester having a chiral center adjacent to the boron, and repetition of the homologation process described in this invention will introduce a second adjacent chiral center, initially in the form of an α-halo boronic ester. If the nucleophile is an alkoxide, for example benzyloxide, the resulting α-alkoxy boronic ester can be homologated similarly to a β-alkoxy-α-halo boronic ester, with a very high degree of control of the absolute chirality of both the α and β carbon atoms. It is believed that such homologation processes may be repeated indefinitely to provide any number of adjacent chiral carbon atoms with a high degree of absolute control. Since it is known from Matteson et al., *J. Am. Chem. Soc.*, Vol. 102, pp 7590–7591 (1980) that one chiral directing group, the (+)-pinanediol group, can be cleaved from the boron and replaced by its enantiomer, (−)-pinanediol, the absolute chirality of each carbon atom introduced is a matter of choice. Finally, the boronic ester group may be replaced essentially stereospecifically with a hydroxyl group by means of oxidation with alkaline hydrogen peroxide, a well established procedure. Alternatively, there are known methods for replacing the boronic ester group by a hydrogen atom (by means of protolysis) or by various other functional groups. As a result of these and other known transformations of α-halo boronic esters and their derivatives, the present invention provides the key step to a wide ranging and broadly useful system of directed chiral synthesis. Useful products which may be prepared by the process of the present invention therefore include not only the insect attractants specifically named, but also potentially include a variety of other insect attractants, antibiotics, pharmaceuticals, and other substances having significant biological activity, where the biological activity depends upon the absolute configuration of one or more chiral carbon atoms in the molecule.

Except for the presence of the Lewis acid catalyst during the conversion of the various boronate complexes, the present process is conducted in the known manner discussed above. That the present invention represents a substantial improvement over the above-discussed uncatalyzed process is shown by the data on yields and diastereoselectivities shown in the following table:

TABLE 1

Yields and Diastereoselectivities in Homologations of (+)-Pinanediol Boronic Esters, $R^1$—$BO_2C_{10}H_{16}(+)$ (IX'), to (αS)—α-Chloro Boronic Esters, $R^1$—$CHCl$—$BO_2C_{10}H_{16}(+)$ (XII) and (αR)—α-Chloro Boronic Esters (XIII)

| $R^1$ of (IX) and (XII) | Catalyst | % Yield of (XII) | % Diastereoselectivity[a] | Analysis[b] |
|---|---|---|---|---|
| CH₃ | None | 57 | 74 | A |
| CH₃ | ZnCl₂ | 83 | 95.7 | B |
| n-C₄H₉ | None | 61 | 90 | A |
| n-C₄H₉ | ZnCl₂ | 92 | 98.5 | A |
| (CH₃)₂CHCH₂ | None | 30 | 88 | B |
| (CH₃)₂CHCH₂ | ZnCl₂ | 89 | 99.5 | B |
| (CH₃)₂CHCH₂ | FeCl₃ | 55 | (not determined) | |
| C₆H₅CH₂ | None | 75 | 92.5 | A |
| C₆H₅CH₂ | ZnCl₂ | 99 | 99.5 | B |

[a] 100 × (XII)/[(XII) + (XIII)]...(IX').
[b] A: The (IX) was reacted with a Grignard reagent and the resulting boronic ester was oxidized with hydrogen peroxide to an alcohol of known absolute configuration and rotation as described in Matteson et al., J. Am. Chem. Soc., Vol. 102, pp 7590–7591 (1980).
B: 200 MHz proton NMR data on (IX') or a derivative compared with known data for both diastereomers.

Other data, in addition to that set forth in Table 1, indicates the superiority of the procedure of this invention over the previously known process. For example, alkoxy substituents in the group $R^1$ of the boronic esters (IX) are known to slow the rearrangement of the derived borates (α-halo boronic esters). See Matteson et al., *J. Am. Chem. Soc.*, Vol. 102, pp 7588–7590 (1980). Accordingly, it is difficult to obtain satisfactory yields, and in some cases any yield at all, of (XII) from (+)-pinanediol boronic esters (IX) bearing an alkoxy substituent when the above-discussed uncatalyzed process is employed. On the contrary, as can be seen by the examples hereinbelow, by using a Lewis acid catalyst in the conversion of the boronate complexes, for example, using $ZnCl_2$ in an amount of from about 0.5–1.0 mol per mol of boronate complex, high yields of boronic esters bearing alkoxy substituents can be obtained.

Another type of improvement resulting from the present process can be seen in the conversion of (+)-pinanediol benzeneboronate ($R^1 = C_6H_5$) to (+)-pinanediol (αS)-α-chlorobenzylboronate, a transformation which gave satisfactory yields and diastereoselectivities by the process disclosed in Matteson et al., *J. Am. Chem. Soc.*, Vol. 102, pp 7590–7591 (1980), except that the labile product could not be isolated and purified. In contrast, this α-chloro boronic ester prepared by the Lewis acid catalyzed process of the present invention proved to be a crystalline compound, easily separated from the small amount of diastereomer present by recrystallization.

It is to be understood, of course, that the process of the present invention is not restricted to the use of pinanediol-containing boronic esters as the chiral directing group, and that a variety of other chiral directing groups may be used. For example, it has been shown that a boronic ester prepared from (R,R)-2,3-butanediol is readily homologated by dichloromethyllithium with the aid of zinc chloride catalysis to produce an (αS)-α-chloro boronic ester in high yield and diastereoselectivity.

The major features of this invention may be understood more fully by means of the illustrative examples which follow, in addition to the extensive experimental data already given. It will be appreciated, of course, that these examples and the foregoing data are intended to be typical but not to be limiting in scope. Unless otherwise indicated, throughout this specification and claims, all temperatures are in degrees Centigrade and all parts and percentages are by weight.

EXAMPLE 1

Preparation of (+)-Pinanediol (1S)-1-Chloroethane-1-boronate.

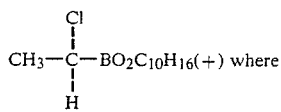

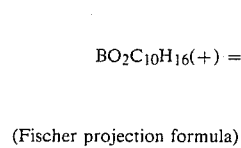

(Fischer projection formula)

Dichloromethyllithium was prepared in an argon-filled flask by addition of 28 mmol of n-butyllithium in hexane to 2 mL of dichloromethane in 40 mL of tetrahydrofuran stirred at −100° C. under argon. A solution of 4.87 g (25.2 mmol) of (+)-pinanediol methaneborate in 15 ml. of diethyl ether was injected from a syringe into the cold slurry of dichloromethyllithium, resulting in dissolution of the solid.

The cap was removed briefly from the argon-filled flask and 1.89 g (13.9 mmol) of finely powdered anhydrous zinc chloride was added quickly from another argon-filled container. (The zinc chloride has been prepared in powdered form by heating commercial reagent grade crystalline anhydrous zinc chloride while stirring with a magnetic stirrer under vacuum at 0.01–0.02 torr at temperatures up to 100° C.) The mixture was stirred under argon and allowed to warm to room temperature (20°–25° C.), then stirred overnight. The solvents were distilled under vacuum below 30° C., the residue was treated with petroleum ether (bp 30°–60° C.) followed by water, the aqueous phase was extracted with additional petroleum ether, and the combined petroleum ether extracts were concentrated under vacuum. Distillation of the residue yielded 0.63 g (13%) of unchanged (+)-pinanediol methaneborate followed by 4.7 g (83%) of the product, (+)-pinanediol (1S)-1-chloroethaneborate, bp 80°–82° C. (0.2 torr). Anal. Calcd. for $C_{12}H_{20}BClO_2$: C, 59.42; H, 8.31; B, 4.46; Cl, 14,62. Found: C, 59.21; H, 8.23; B, 4.33; Cl, 14.76%. The diastereomeric purity of the product was estimated from comparison of the 200 MHz proton NMR spectrum with that of a sample which had been epimerized by treatment with lithium chloride to provide a mixture with the (1R)-isomer. The mixture showed a pair of peaks at 226.74 and 237.67 Hz (from the tetramethylsilane reference) resulting from the (R)-isomer in addition to the corresponding pair at 229.14 and 240.09 Hz due to the (S)-isomer. The original reaction product showed predominantly the peaks of the (S)-isomer with weak shoulders corresponding to the (R)-isomer in the amount of approximately 5%. Further evidence for the diastereomeric purity was provided by treatment of the reaction product, (+)-pinanediol (1S)-1-chloroethaneboronate, with lithiohexamethyldisilazane, followed by acetic acid and acetic anhydride to yield (+)-pinanediol (R)-1-acetamidoethane-1-boronate. From the NH peaks in the NMR at δ 9.8 and 9.2 and comparison with a mixture enriched in the (S)-epimer, the diastereomeric purity of the (R)-isomer was estimated to be 95.7%. Finally, the absolute configuration of the newly introduced chiral carbon atom was determined by converting the (+)-pinanediol (1S)-1-chloroethane-1-boronate to (+)-(R)-1-phenylethyl acetate by successive treatment with phenylmagnesium bromide, hydrogen peroxide and acetic anhydride. The diastereomeric purity estimated from the optical rotation of the 1-phenylethyl acetate was 93.3%.

EXAMPLE 2

Preparation of (+)-Pinanediol (1S)-1-Chloro-3-methylbutane-1-boronate.

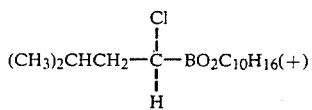

The procedure of Example 1 was followed, with 0.708 g (3.0 mmol) of (+)-pinanediol 2-methylpropane-1-boronate in place of the (+)-pinanediol methaneborate and with the other reagents scaled proportionately, 3.15 mmol of dichloromethyllithium and 0.24 g (1.76 mmol)

of anhydrous zinc chloride, and the quantities of solvents scaled down to 4 mL of tetrahydrofuran and 2 mL of ether. The product was distilled in a short path apparatus at 95° C. (0.1 torr) and weighed 0.822 g. NMR analysis indicated its composition to be 10% unchanged (+)-pinanediol 2-methylpropane-1-boronate and 90% (+)-pinanediol (1S)-1-chloro-3-methylbutane-1-boronate. Treatment of this crude product with lithiohexamethyldisilazane followed by acetic acid and acetic anhydride as in Example 1 yielded (+)-pinanediol (1R)-1-acetamido-3-methylbutane-1-boronate. The crude material was analyzed by 200 MHz NMR and found to contain the (1R) and (1S) isomers in the ratio 200:1, based on the NH peaks which appear near δ 9.0 and 8.3 for the respective isomers. The identity of the peak due to the minor isomer was confirmed by addition of a sample enriched in that isomer.

EXAMPLE 3

Preparation of (+)-Pinanediol (1S)-1-Chloro-2-phenylethane-1-boronate.

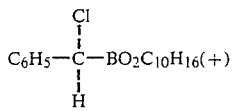

The procedure of Example 1 was followed, with 6.75 g (25 mmol) of (+)-pinanediol benzylboronate, 27 mmol of dichloromethyllithium, 30 mL of tetrahydrofuran, 20 mL of diethyl ether, and 1.75 g (12.8 mmol) of anhydrous zinc chloride. NMR analysis indicated that the reaction was complete after 3.5 hr at 20°–25° C. When the petroleum ether extracts were concentrated, the residue crystallized and 7.9 g. (99%) was recovered. The recovered product was shown to be pure (+)-pinanediol (1S)-1-chloro-2-phenylethane-1-boronate by 200 MHz proton NMR analysis, with less than 0.5% of the (1R) isomer present. This was confirmed by comparison with an epimerized sample consisting of approximately equal amounts of the (1S) and (1R) isomers, which show distinctive peaks in the multiplet near δ 3.65 (especially the (1R) peaks at 718.6 Hz and 735.2 Hz and the (1S) peaks at 722.4 and 738.6 Hz downfield from tetramethylsilane). (For the preparation of this compound without the aid of zinc chloride catalysis, see Matteson et al., *J. Am. Chem. Soc.*, Vol. 103, pp 52–5242 (1981).

EXAMPLE 4

Preparation of (3S,4S)-4-Methyl-3-heptanol.

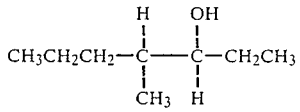

As disclosed in Pearce et al., *J. Chem. Ecol.*, 1, p 115 (1975), this compound is known to be a component of the pheromone of the European elm bark beetle, *Scolytus multistriatus*. The present synthesis began with (+)-pinanediol propane-1-boronate, which was converted to (+)-pinanediol (1S)-1-chlorobutane-1-boronate by the procedure outlined in Example 1. This compound was then treated with methylmagnesium bromide (stoichiometric amounts of reactants were used, with 60 ml of tetrahydrofuran solvent for 24 mmol), and kept at 20° C. overnight. The isomeric purity of the (+)-pinanediol (2S)-pentane-2-boronate was confirmed by oxidation with alkaline hydrogen peroxide to (S)-2-pentanol, rotation [α]$^{25}$589 +12.86° (c 1.5%, ethanol), which corresponds to 98.2% enantiomeric excess, 99.1% diastereomeric purity of the precursor. (+)-Pinanediol (2S)-pentane-2-boronate was converted to (+)-pinanediol (1S,2S)-1-chloro-2-methylpentane-1-boronate by the procedure outlined in Example 1. This compound was then treated with ethylmagnesium bromide as described above to yield (+)-pinanediol (3S,4S)-4-methylheptane-3-boronate. This material which was chromatographed on silica with 20% ethyl acetate in hexane and distilled in a short path apparatus under high vacuum, and which was prepared in a yield of 86.5% (based on the pentane-2-boronate), was oxidized with alkaline hydrogen peroxide to yield (3S,4S)-4-methyl-3-heptanol, bp 102°–104° C. (95 torr), [α]$^{24}$589 −19.84° (c 4.4%, hexane). Attempts to detect any diastereomer by standard NMR methods failed. Properties reported for this compound in Mori, *Tetrahedron*, 33, pp 289–294 (1977) are bp 105°–108° C. (102 torr), [α]$^{22}$D −21.7° (c 0.57%, hexane).

EXAMPLE 5

Preparation of exo-Brevicomin.

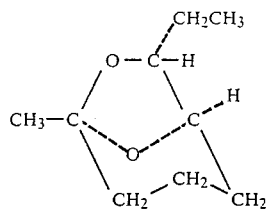

This compound is the major attractive component of the pheromone of the western pine beetle, *Dendroctonus brevicomis*. The present synthesis began with the ethylene ketal of 5-chloro-2-pentanone, which was converted to the Grignard reagent in the usual manner. The resulting intermediate was treated with trimethyl borate, and the resulting boron compound was esterified with (−)-pinanediol to yield the ethylene ketal of (−)-pinanediol 4-ketopentane-1-boronate, alternatively named (−)-pinanediol 4-(ethylenedioxy)pentane-1-boronate, bp 123°–124° C. (0.05 torr), [α]$^{21}$546 −17.03° (c 9.9%, chloroform), anal. C, H. B. This compound was treated according to the procedure of Example 1 to yield (−)-pinanediol (1R)-1-chloro-5-(ethylenedioxy)-hexane-1-boronate, which was partially purified by concentration of the original reaction mixture, treatment with petroleum ether followed by saturated aqueous ammonium chloride, and concentration of the petroleum ether extract. The content of (1S) isomer was found to be less than 0.5% by 200 MHz NMR comparison with an epimeric mixture prepared from the corresponding ethylene glycol boronic ester (racemic) by transesterification with pinanediol. This crude product was treated with lithium benzyloxide to yield (−)-pinanediol (1S)-1-benzyloxy-5-(ethylenedioxy)-hexane-1-boronate, which was chromatographed on silica with 20% ethyl acetate in hexane. The yield was 94% (based on the 4-(ethylenedioxy)pentane-1-boronate), anal. C, H, B. By 200 MHz NMR analysis, the diastereomeric purity of this compound was approximately 98%. This compound was treated with dichloromethyllithium according to the procedure of Example 1 to yield (—)-pinanediol (1R,2R)-1-chloro-2-benzyloxy-6-(ethylenedioxy)-heptane-1-boronate, which was partially purified as described for the preceding α-chloro boronic ester in this example. This material was treated with ethylmagnesium bromide according to the usual method, as discussed in Example 4, but requiring 36 hr at 20°–25° C. for completion of the reaction, to yield (—)-pinanediol (3R,4R)-4-benzyloxy-8-(ethylenedioxy)-3-boronate; the latter being isolated by work up with petroleum ether and saturated ammonium chloride and chromatography on silica with 20% ethyl acetate in hexane. The yield of this compound was 82% (based on the 1-benzyloxy-5-(ethylenedioxy)-hexane-1-boronate), anal. C, H, B, $[\alpha]^{23}_{546}$ −2.09° (c 4.8%, chloroform). Oxidation of this compound with alkaline hydrogen peroxide followed by hydrolysis of the ethylene ketal with sulfuric acid-treated silica yielded (3R,4R)-4-benzyloxy-8-oxo-3-nonanol (79%); the NMR, infrared, and mass spectra of which were in agreement with values reported in Sherk et al., *J. Org. Chem.*, Vol. 47, pp 932–935 (1982). However, the material prepared in this example had $[\alpha]^{23}_{589}$ −13.1° (c 4.3%, chloroform), and crystallized, from hexane, mp 30°–31° C., which removed all evidence of impurities from the 200 MHz NMR spectrum. Material which had not been recrystallized was converted to exo-brevicomin by the method disclosed in the above Sherk et al. article and had $[\alpha]^{23}_{589}$ +81.06° (c 1.4%, ether). Gas chromatographic analysis indicated the presence of 2% of the diastereomer, endo-brevicomin, and 200 MHz NMR analysis indicated 3% endo-brevicomin. The identification of exo-brevicomin as the principal component of the attractant pheromone of *Dendroctonus brevicomis* and the physical properties of exo-brevicomin and its endo isomer have been reported previously in Bellas et al., *Tetrahedron*, 25, pp 5149–5153 (1969) and Mori, *Tetrahedron*, 30, pp 4223–4227 (1974). (Bellas, Brownlee, and Silverstein).

EXAMPLE 6

Homologation of (R,R)-2,3-Butanediol Butane-1-boronate.

Butaneboronic acid was esterified with (—)-(R,R)-2,3-butanediol by stirring the reactants in ether until dissolved and adding hexane to aid separation of water and any excess diol. The resulting (R,R)-2,3-butanediol butaneboronate was purified by distillation at 43°–45° C. (5 torr). This material was then added to dichloromethyllithium and the mixture treated with zinc chloride according to the general procedure of Example 1. Concentration of the reaction mixture, treatment with water, and extraction into petroleum ether, followed by concentration under vacuum yielded crude α-chloropentaneboronic ester. The crude ester was not isolated, but immediately was treated with lithiohexamethyldisilazane followed by acetic acid and acetic anhydride according to the procedure of Example 2 to yield 80% of crude crystalline (R,R)-2,3-butanediol 1-acetamidopentane-1-boronate. The 200 MHz NMR spectrum of this material indicated two overlapping NH peaks at δ 9.7, and a curve fitting analysis indicated that the major diastereomer constituted 94–95% of the material. This material was then transesterified by treatment with (+)-pinanediol to produce the known (+)-pinanediol 1-acetamido-1-pentaneboronate, which was chromatographed on a short column of silica with ether as the eluant, mp 140°–141° C. From the two NH peaks near δ 7.3 in the 200 MHz proton NMR spectrum and comparison with known diastereomer samples, the major diastereomer was found to constitute 95–96% of this product, and was identified as (+)-pinanediol (1R)-1-acetamidopentane-1-boronate. Because the mechanism of replacement of the chlorine requires inversion of the carbon atom, it was concluded that the α-chloro boronic ester intermediate in this sequence is (R,R)-2,3-butanediol (1S)-1-chloropentane-1-boronate, and that the reaction is approximately 95% diastereoselective for this isomer.

EXAMPLE 7

Homologation of (+)-Pinanediol Benzeneboronate with (1,1-Dichloroethyl)lithium.

1,1-Dichloroethyllithium was prepared by treating 5 mmol of 1,1-dichloroethane with 5.5 mmol of n-butyllithium in 10 mL of THF at −100° C., the procedure being similar to that of Example 1 for generating (dichloromethyl)lithium. (+)-Pinanediol benzeneboronate (1.26 g, 4.9 mmol) in 3 mL of ether was added to the slurry of (1,1-dichloroethyl)lithium. After stirring 40 hr at room temperature, the solvent was distilled. Ether was added to the residue and the precipitated lithium chloride was filtered. The product was distilled bulb to bulb at 100° C. (0.1 torr). The yield was 1.26 g. Both 200 MHz NMR and gas chromatographic analysis indicated that the product was a mixture containing approximately 30% of the homologated product, (+)-pinanediol 1-chloro-1-phenylethane-1-boronate, and that the remainder was unchanged (+)-pinanediol benzeneboronate.

EXAMPLE 8

Ferric Chloride as Catalyst.

The procedure of Example 2 was followed, substituting 0.5593 g (3.4 mmol) of anhydrous ferric chloride in place of the zinc chloride, with the other reactants being in the amounts as in Example 2. The product was isolated by short path distillation and found to consist of a mixture of 55% (+)-pinanediol (1S)-1-chloro-3-methylbutane-1-boronate and 45% unchanged (+)-pinanediol 2-methylpropane-1-boronate by 60 MHz proton NMR analysis.

EXAMPLE 9

(+)-Pinanediol (S)-1-Chloropentane-1-boronate from (+)-Pinanediol Butane-1-boronate, Dichloromethane, and Lithium Dicyclohexylamide.

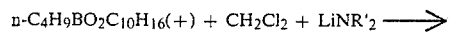

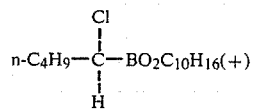

A solution of 3 mmol of lithium dicyclohexylamide was prepared from 3 mmol of 1.6M butyllithium in hexane and 3 mmol of dicyclohexylamine in 5 mL of tetrahydrofuran. This solution was cooled with an ice bath and added dropwise under argon to a stirred solution of 0.71 g (3 mmol) of (+)-pinanediol butane-1-boronate in 8 mL of tetrahydrofuran; cooled with an ice bath. The cooling bath was removed and the mixture was kept at room temperature (20°–25° C.) for 18 hr. The solution was concentrated under vacuum and 50 mL of petroleum ether followed by dilute (2M) sulfuric acid was added. The phases were separated and the aqueous phase was further extracted with petroleum ether, and the combined petroleum ether extract was passed through a short column of silica, which was washed with addititonal petroleum ether, and then concentrated under vacuum. The residue weighed 0.668 g and was shown to consist of a mixture of 34% unchanged (+)-pinanediol butane-1-boronate and 53% (+)-pinanediol 1-chloropentane-1-boronate (41% yield) with the remainder an unidentified byproduct by 200 MHz NMR analysis. The ratio of (1S)- to (1R)-1-chloropentane-1-boronate was found to be 94:6 by NMR analysis.

EXAMPLE 10

(+)-Pinanediol (S)-1-Chloropentane-1-boronate from (+)-Pinanediol Butane-1-boronate, Dichloromethane, Lithium Dicyclohexylamide, and Zinc Chloride.

The procedure of Example 9 was repeated, except that after completion of the addition of the lithium dicyclohexylamide to the solution of (+)-pinanediol butane-1-boronate and dichloromethane, one equivalent (3 mmol) of anhydrous zinc chloride was added to the mixture. The yield of (+)-pinanediol 1-chloropentane-1-boronate was 48%, of which 96% was (1S)-1-chloropentane-1-boronate and 4% was (1R)-1-chloropentane-1-boronate, based on 200 MHz NMR analysis.

As can be seen from the foregoing examples, the rearrangement of the various boronate complexes to their respective boronic esters may take place over a period from as short as a few hours to as long as a few days. For the most part, however, when the boronate complexes are contacted at about room temperature with a Lewis acid in accordance with the present invention, the conversion or rearrangement to the desired boronic esters takes place in from about 3-40 hrs.

In accord with usual chemical principles, it is expected that somewhat higher temperatures than 30° C. will accelerate the reaction without significantly altering the result, as demonstrated for the uncatalyzed process at temperatures up to 80°-120° C., Matteson and Majumdar, *J. Am. Chem. Soc.*, Vol. 102, pp 7588-7590 (1980). For groups $R^1$ which have high migratory aptitude, including vinyl and phenyl, it has been found that rearrangements of (I) to (II) occur within an hour at temperatures in the range −40° to 0° C. in the presence of zinc chloride. The times and temperatures mentioned are for pinanediol boronic esters. It is expected that less sterically hindered boronic esters will react faster, and optimum temperatures may be somewhat lower.

Accordingly, in accordance with the present invention, it has been found that the borate complexes normally are contacted with a Lewis acid catalyst at a temperature in range of about −40° C. to +80° C.

What is claimed is:

1. In a process for preparing boronate esters having the general structure

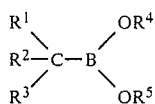
II from boronate complexes having the general structure,

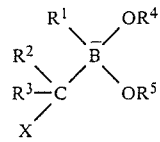
I where each of $R^1$, $R^4$ and $R^5$, independently, is an organic group selected from the group consisting of aliphatic, aromatic and functionally substituted aliphatic and aromatic groups, where X is a nucleofugic group, where $R^2$ is a nucleofugic group or an organic group selected from the group consisting of aliphatic, aromatic and functionally substituted aliphatic or aromatic groups, $R^3$ is hydrogen or a group selected from the same groups as $R^2$, and where $R^4$ and $R^5$ may be the same or different and may be linked such that the resulting $OR^4$—$R^4O$ boronic ester group is cyclic, the improvement which comprises contacting the boronate complex (I) in solution in the temperature range −40° to +80° C. with a Lewis acid catalyst, having an acid strength which is sufficiently high to combine with the nucleofugic group X to form a complex, but which is low enough so as not to destory the groups $OR^4$, $OR^5$ and $OR^4$—$R^5O$, said catalyst having an acid strength on the order of that characteristic of ferric chloride, ferric bromide, zinc chloride and zinc bromide.

2. The process of claim 1, wherein the nucleofugic group X is selected from chlorine and bromine.

3. The process of claim 2, wherein the Lewis acid catalyst is selected from zinc chloride, zinc bromide, ferric bromide and ferric chloride and mixtures thereof.

4. The process of claim 3, wherein the Lewis acid catalyst is present in an amount of from about 0.5–1.0 mol per mol of the boronate complex (I).

5. In a process for the rearrangement of chiral boronate complexes of the general structure

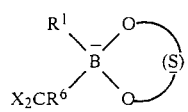

where $R^1$ is an organic group selected from the group consisting of aliphatic, aromatic and functionally substituted aliphatic and aromatic groups, where X is chlorine or bromine, where $R^6$ is H or lower alkyl, and the boronic ester group

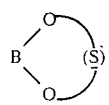

is any chiral group that is (S)-directing, to form chiral boronic esters of the general structure

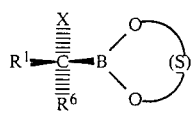

the improvement which comprises contacting the chiral boronate complex in solution at about 0°-30° C. with a Lewis acid catalyst having sufficient acid strength to form a complex with X, but insufficient acid strength to destroy the chiral directing group, said catalyst having an acid strength on the order of that characteristic of ferric chloride, ferric bromide, zinc chloride and zinc bromide.

6. The process of claim 5 wherein said Lewis acid is selected from zinc chloride, zinc bromide, ferric bromide and ferric chloride and mixtures thereof.

7. In a process for the rearrangement of chiral boronate complexes of the general structure

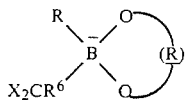

to chiral boronic esters of the general structure

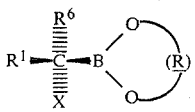

where $R^1$ is an organic group selected from aliphatic, aromatic and functionally substituted aliphatic and aromatic groups, where X is chlorine or bromine, where $R^6$ is H or lower alkyl, and the boronic ester group

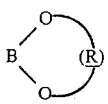

is a chiral group that is (R)-directing, the improvement which comprises contacting the chiral boronate complex in solution at about 0°-30° C. with a Lewis acid catalyst hsving sufficient acid strength to form a complex with X, but insufficient acid strength to destroy the chiral directing group, said catalyst having an acid strength on the order of that characteristic of ferric chloride, ferric bromide, zinc chloride and zinc bromide.

8. The process of claim 7 wherein said Lewis acid is selected from zinc chloride, zinc bromide, ferric bromide and ferric chloride and mixtures thereof.

9. In a process for preparing α-haloboronic esters wherein a boronic ester of the general structure

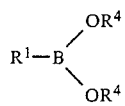

is converted to a boronate complex of the general structure

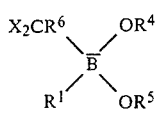

which, in turn, is rearranged to an α-haloboronic ester of the general structure

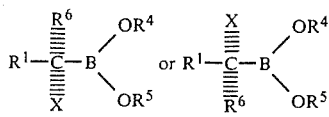

where each of $R^1$, $R^4$ and $R^5$, independently, is an organic group selected from the group consisting of aliphatic, aromatic and functionally substituted aliphatic and aromatic groups, where $R^6$ is H or alkyl, where $R^4$ and $R^5$ may be the same or different and may be linked such that the resulting $OR^4$—$R^5$—O boronic ester group is cyclic, and where X is chloro or bromo, the improvement which comprises rearranging the boronate complex by contacting the same in a suitable solvent medium with a Lewis acid catalyst and at temperature of about 0°-30° C., said Lewis acid being of sufficient acid strength to form a complex with X, yet of insufficient acid strength to destroy the groups $OR^4$, $OR^5$ and $OR^4$—$R^5O$, said catalyst having an acid strength on the order of that characteristic of ferric chloride, ferric bromide, zinc chloride and zinc bromide.

10. The process of claim 9 wherein said Lewis acid catalyst is selected from the group consisting of zinc chloride, zinc bromide, ferric bromide and ferric chloride.

11. The process of claim 10, wherein the boronic ester is converted to the boronate complex by reaction at about −70° to −100° C. with a dihaloalkylmetal of the general structure $$M^+CHX_2^-$$

where the cation $M^+$ is a member selected from the group consisting of lithium, sodium and potassium.

12. The process of claim 11, wherein the boronic ester is selected from the group consisting of (+)-pinanediol boronic esters and (−)-pinanediol boronic esters.

13. The process of claim 12, where X is chloro and M is lithium.

14. The process of claim 6, wherein the chiral boronate complex has the general structure

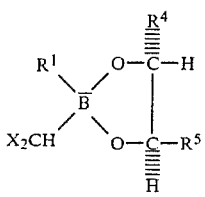

where each of $R^4$ and $R^5$, independently, is an organic group selected from the group consisting of aliphatic, aromatic and functionally substituted aliphatic and aromatic groups.

15. The process of claim 8, wherein the chiral boronate complex has the general structure

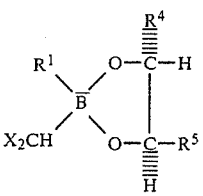

where each of $R^4$ and $R^5$, independently, is an organic group selected from the group consisting of aliphatic, aromatic and functionally substituted aliphatic and aromatic groups.

16. A process for preparing α-haloboronic esters of the general structure

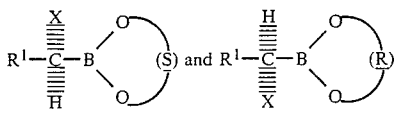

where $R^1$ is an organic group selected from the group consisting of aliphatic, aromatic and functionally substituted aliphatic and aromatic groups, X is bromo or chloro,

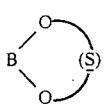

is any chiral group that is (S)-directing, and

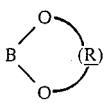

is any chiral group that is (R)-directing, which comprises reacting at about 0° C. a boronic ester of the general structure

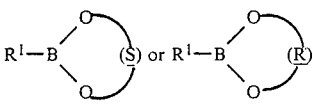

with $CH_2X_2$ and a strong sterically hindered base, to form a boronate complex of the general structure

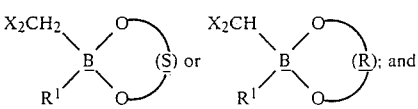

rearranging the boronate complex to the desired α-haloboronic ester by contacting said complex in a suitable solvent medium at about 0°–30° C. with a Lewis acid catalyst having a sufficient acid strength to complex with X, yet an insufficient acid strength to descroy the

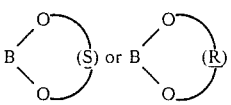

group, said catalyst having an acid strength on the order of that characteristic of ferric chloride, ferric bromide, zinc chloride and zinc bromide.

17. The process of claim 16, wherein the sterically hindered base is an alkali metal dialkylamide having the general structure $NMR^7R^8$ where M is a member selected from the group consisting of lithium, solidum and potassium, and each of $R^7$ and $R^8$, which may be the same or different, is a member selected from primary and secondary alkyl groups; and wherein the Lewis acid is selected from zinc chloride, zinc bromide, ferric bromide and ferric chloride.

18. The process of claim 17, wherein the alkalimetal dialkylamide is selected from the group consisting of lithium dicyclohexylamide and lithium diisopropylamide.

19. The process of claim 16 wherein the sterically hindered base is an alkali metal bis(trialkylsilyl)amide having the general structure $MN(Si R^9_3)_2$ where M is a member selected from the group consisting of lithium, sodium, and potassium and each of the $R^9$ members, which may be the same or different, is selected from alkyl or aryl groups.

20. The process of claim 19, wherein the alkali metal bis(trialkylsilyl)amide is selected from the group consisting of lithium, sodium, or potassium bis(trimethylsilyl)amide.

21. The process of claim 16 wherein the sterically hindered base is lithiotriphenylmethane.

22. A process for preparing (+)-pinanediol (αS)-α-haloboronic esters of the general structure

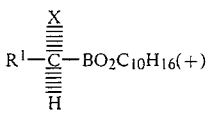

where $R^1$ is an organic group selected from the group consisting of aliphatic, aromatic and functionally substituted aliphatic and aromatic group, and where X is a member selected from the group consisting of chloro and bromo, which comprises:

reacting at about 0° C. a (+)-pinanediol ester general structure

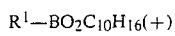

$R^1-BO_2C_{10}H_{16}(+)$ with a dihalomethane and a strong, sterically hindered base to form a boronate complex of the general structure

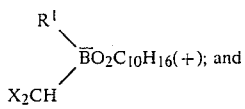

rearranging said complex to the desired (+)-pinanediol (αS)-α-haloboronic ester by contacting said complex in a suitable solvent at about 0°–30° C. with a Lewis acid catalyst having a sifficient strength to complex with X, yet an insufficient acid strength to destroy the $BO_2C_{10}H_{16}(+)$ group, said catalyst having an acid strength on the order of that characteristic of ferric chloride, ferric bromide, zinc chloride and zinc bromide.

23. The process of claim 22, wherein the sterically hindered base is an alkali metal dialkylamide of the general structure $MNR^7R^8$ where M is a member selected from the group consisting of lithium, sodium and potassium, and each of $R^7$ and $R^8$, which may be the same or different, is a member selected from the group consisting of primary and secondary alkyl groups.

24. The process of claim 23, wherein the Lewis acid is selected from the group consisting of zinc chloride, zinc bromide, ferric bromide and ferric chloride.

25. A process for preparing (+)-pinanediol ($\alpha$R)-$\alpha$-halo boronic esters of the general structure

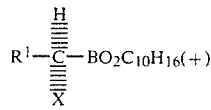

where $R^1$ is an organic group selected from the gorup consisting of aliphatic, aromatic and functionally substituted aliphatic and aromatic groups, and where X is a member selected from the group consisting of chloro and bromo, which comprises:

reacting at about 0° C. a (+)-pinanediol ester having the general structure

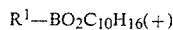

with a dihalomethane and a strong, sterically hindered base to form a boronate complex of the general structure

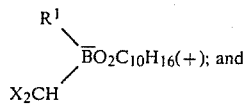

rearranging said complex to the desired (+)-pinanediol ($\alpha$R)-$\alpha$-haloboronic ester by contacting said complex in a suitable solvent at about 0°–30° C. with a Lewis acid catalyst having a sufficient acid strength to complex with X, yet an insufficient acid strength to destroy the $BO_2C_{10}H_{16}$(+) group, said catalyst having an acid strength on the order of that characteristic of ferric chloride, ferric bromide, zinc chloride and zinc bromide.

26. The process of claim 25, wherein the sterically hindered base is an alkali metal dialkylamide of the general structure

where M is a member selected from the group consisting of lithium, sodium and potassium, and each of $R^7$ and $R^8$, which may be the same or different, is a member selected from the group consisting of primary and secondary alkyl groups.

27. The process of claim 25, wherein the Lewis acid is selected from the group consisting of zinc chloride, zinc bromide, ferric bromide and ferric chloride.

* * * * *